United States Patent
Simon et al.

[11] Patent Number: 6,141,480
[45] Date of Patent: Oct. 31, 2000

[54] TECHNIQUE FOR LOCATION OF EMBEDDED FIBER OPTIC SENSORS

[75] Inventors: Wayne R. Simon, Baltimore; William R. Pogue, III, Gambrills, both of Md.

[73] Assignee: The United States of America as represented by the Secretary of the Navy, Washington, D.C.

[21] Appl. No.: 09/246,174

[22] Filed: Oct. 29, 1998

[51] Int. Cl.[7] .................................................. G02B 6/00
[52] U.S. Cl. ............................ 385/147; 385/12; 385/13; 73/800; 250/227.16; 250/227.14; 356/32; 356/345
[58] Field of Search .................................. 385/12, 13, 37, 385/147; 250/227.16, 227.14, 227.18, 227.17, 231.1; 356/32, 33, 356, 345; 73/800, 802

[56] References Cited

U.S. PATENT DOCUMENTS 4,836,030  6/1989  Martin ........................................ 73/800
5,477,323  12/1995  Andrews et al. ...................... 385/12 X

*Primary Examiner*—Phan T. H. Palmer
*Attorney, Agent, or Firm*—Barry A. Edelberg; Charles J. Stockstill

[57] ABSTRACT

This invention describes a process for locating the position, orientation and depth of fiber optic sensors embedded in a composite material. The process encompasses the coating of the fiber optic sensor with an X-ray opaque material prior to embedding the sensor in a composite material and then mapping the composite material using radiographic techniques to accurately establish the location, orientation and depth of the sensor. A radiographic film or electronically recorded record of the exact placement of the sensors is prepared that may be referenced during machining operations, correlation of test results and accurate mapping of the structure.

5 Claims, 1 Drawing Sheet

TECHNIQUE FOR LOCATION OF EMBEDDED FIBER OPTIC SENSORS

BACKGROUND OF THE INVENTION

1. Field of the Invention

This invention pertains generally to the location of fiber optic sensors embedded in a material and more specifically to the location of embedded fiber optic sensors by the use of radiographic inspection.

2. Description of the Related Art

The purpose of embedding fiber optic sensors in materials is to accurately measure a specific material property at a specific location in the composite specimen. To accomplish this, the fiber optic sensor (FOS) must be placed precisely in the desired location (including depth or layer), and ingress of the optical fiber leads must be accomplished with a minimum of risk to the optical fiber and host composite part. The position of the sensor must be determined accurately within the finished product.

Optical fiber sensor systems come in many configurations and have the ability to measure a wide range of material properties and environmental conditions. Fiber optic sensors may be multiplexed (many sensors on a single fiber optic cable), and the sensor length may vary from microns to kilometers, a factor which is wholly dependent on the application and measureand of interest. Fiber optic sensors may be of intrinsic or extrinsic design. Intrinsic fiber optic sensors or all-fiber fiber optic sensors, are sensors whose light throughput properties are modulated by an external environmental condition.

Intrinsic sensors often are indistinguishable from the parent fiber; i.e., it is impossible to tell where the sensor begins and ends on the fiber optic cable. Visual indicators, such as ink marks, may be used to locate the sensor bodies during fabrication, but these become useless once the fiber sensor strand is embedded in a composite part. It is of great importance to be able to locate the position of these sensors with high accuracy. For example, knowledge of sensor position within the part is critical for true knowledge of the strain distribution within the structure, and for correlation of measured strain with an analytical model of the structure.

Ideally, the optical fiber should be disturbed as little as possible by the cure and post cure operations on the part. However, the optical fiber may actually shift within the composite part during curing as the matrix resin liquefies and flows. In thin composite laminates, the position of the optical fiber can sometimes be detected on the surface of the part either tactiley or visually after cure. This allows for avoidance of the optical fiber strand during machining operations. However, the fiber optic sensor is undetectable from the surface of the specimen. This problem is compounded in thicker laminates as there are absolutely no visual indications of the optical fiber position, and one is clueless as to sensor position.

Previous methods for locating intrinsic fiber optic sensors were a "tap test" where the operator taps around on the component with the edge of a coin while watching the sensor output. The method is time consuming, inaccurate, and does not produce a direct record of the sensor location for future reference. There is also no way to determine the orientation of the sensor (at what angle the sensor may be to some reference edge, or surface) or what depth the sensor is within the part.

A second method used for sensors sensitive to temperature is to touch the part with a warm finger, or in the case of thick parts, a soldering iron while watching the sensor output. Again, the method is time consuming, inaccurate, and does not produce a direct record of the sensor location for future reference. As before, there is also no way to determine the orientation of the sensor (at what angle to some reference edge, or surface) or at what depth the sensor is within the part.

BRIEF SUMMARY OF THE INVENTION

The object of this invention is to provide a process whereby embedded fiber optic sensors may be accurately located within a composite material as to position, orientation and depth.

Another objective of this invention is to provide a process for accurately locating embedded fiber optic sensors in composite material that is inexpensive, improves quality control on embedded sensor systems, and does not require any new or unusual non-destructive inspection methods.

These and other objectives are achieved by coating a fiber optic sensor with an X-ray opaque epoxy, or other similar material compatible with the components found within a composite material, prior to embedding the sensor in the composite material and then mapping the composite material using radiographic techniques to establish the location of the embedded sensors in position, orientation and depth. The radiographic films provide permanent record of the exact placement of the sensors that may be referenced during machining operations, correlation of test results, and accurate mapping of the structure.

DETAILED DESCRIPTION OF THE INVENTION

Figure 1:
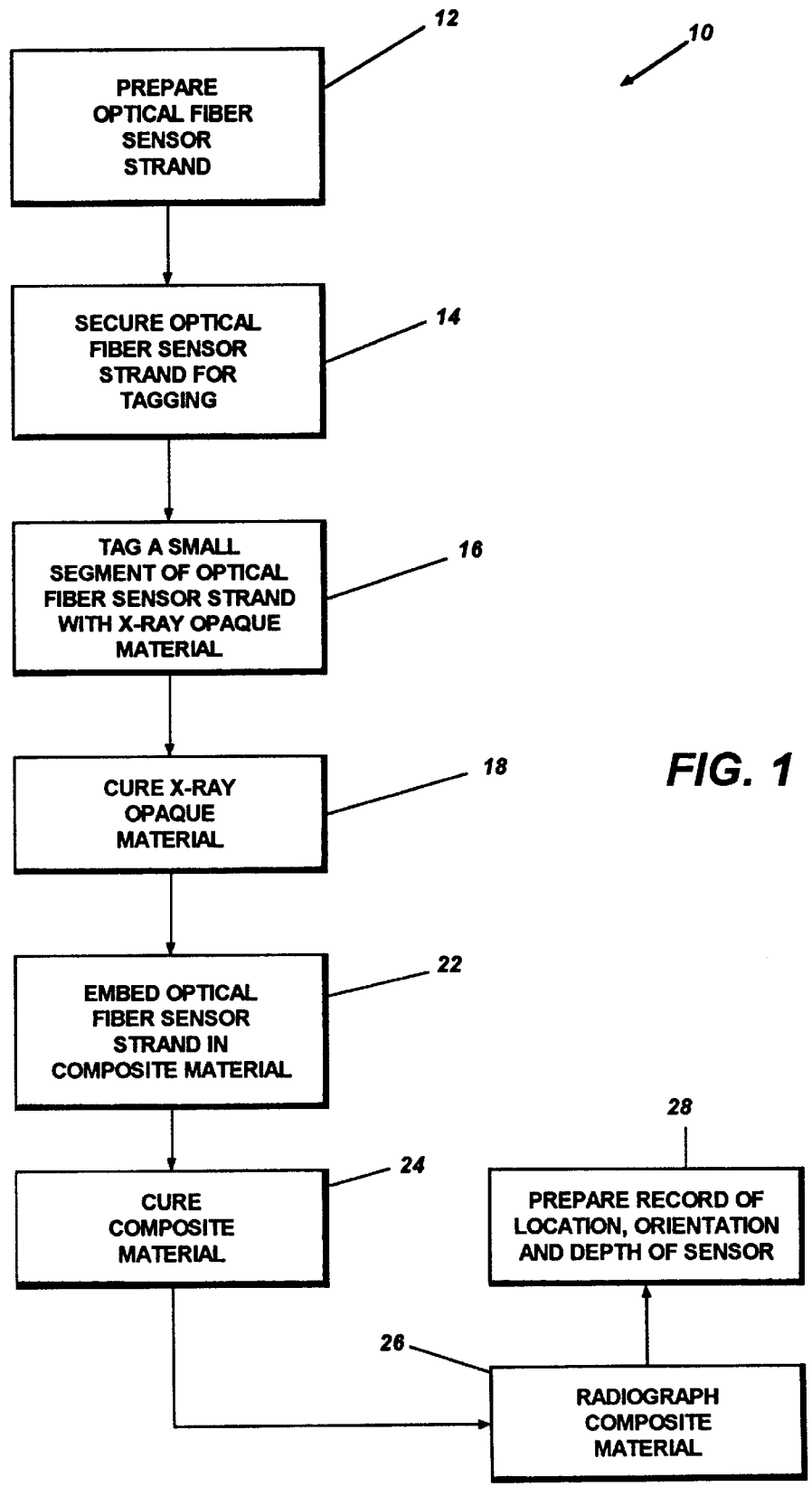
FIG. 1 is a flow chart of the process for detecting fiber optic sensors embedded in a composite material by the use of radiographic techniques.

In the preferred embodiment of this process 10, as shown in the flow chart in FIG. 1, an optical fiber sensor strand is prepared for embedding 12 in a manner well known to those skilled in the art. The fiber is cleaned, preferably with isopropyl alcohol, and end connectors, protective tubing, etc. are applied. A tagging of a small segment of the optical fiber sensor strand, utilizing a technique well known to those skilled in the art, is performed as to the final step before embedding. The ready to be embedded optical fiber is secured to a clean non-stick working surface 14 with a tape, such that a section of the optical fiber containing the sensor is held straight. Preferably, a lead powder X-ray opaque epoxy is mixed according to the manufacturers instructions and the optical fiber is lightly coated 16, or tagged, with a minute quantity of this epoxy at a predetermined distance in each direction along the fiber from the sensor. Lead powder X-ray opaque epoxy is preferred because lead is more opaque to X-ray, however, a silver filled epoxy may be used, or any adhesive material that is compatible with a composite material and its components. The coating 16 is preferably accomplished using a spray technique, applying the tag material in either a manual or automated fashion. Also a felt roller system may be used to apply the tag material 16. The tag material may be applied to the fiber during the fiber draw process directly after the fiber has passed through a coating cup. This may be a computer controlled operation well known to those skilled in the art, and very accurate marking of the sensor locations during the fiber draw and sensor writing is possible.

When the tagging 16 epoxy is fully cured 18, the optical fiber may then be embedded into the composite material 22.

After the composite material, with the embedded fiber optic sensor, has cured 24 a radiographic inspection 26 is made of the finished composite material and a permanent record 28 is made on a suitable recording paper; i.e., photographic film, or electronic medium, i.e., a computer, thereby providing a permanent record of exactly where the embedded sensors are within the composite part and can be referenced for machining operations, correlation of test results, and accurate mapping of the structure. This process is an inexpensive way to improve quality control on embedded sensor systems and does not require any new or unusual nondestructive inspection methods.

Although this invention has been described in relation to an exemplary embodiment thereof, it will be understood by those skilled in the art that still other variations and modifications can be affected in the preferred embodiment without detracting from the scope and spirit of the invention as described in the claims.

What is claimed:

1. A process for locating fiber optic sensors embedded in a composite material comprised of the steps of:

preparing an optical fiber optic strand for embedding by cleaning, attaching end connectors and placing protective coating around the optical fiber strand;

securing the prepared fiber optic sensor strand in such a manner that the fiber optic sensor strand is held straight;

coating the prepared optical fiber optic strand with an X-ray opaque material that is compatible with the composite material and its component materials;

curing the opaque material;

embedding the coated fiber optic sensor in the composite material;

curing the composite material with the fiber optic sensor embedded therein;

radiographing the cured composite material with the fiber optic sensor therein to determine the location of the sensor; and preparing a permanent record of the location, orientation and depth of the embedded fiber optic sensor utilizing information obtained from radiographing the cured composite material.

2. A process, as in claim 1, wherein the X-ray opaque material is a lead powder X-ray opaque epoxy.

3. A process, as in claim 1, wherein the X-ray opaque material is a silver filled epoxy.

4. A process, as in claim 1, wherein the coating is accomplished by use of a manual sprat technique.

5. A process, as in claim 1, wherein the coating is accomplished utilizing an automated spray technique.

* * * * *